United States Patent [19]

Weiss et al.

[11] Patent Number: 4,790,961

[45] Date of Patent: Dec. 13, 1988

[54] THERMALLY REVERSIBLE ORGANIC SOLVENT GELS

[75] Inventors: Richard G. Weiss, Bethesda, Md.; Yih-chyuan Lin, Arlington, Va.

[73] Assignee: Georgetown University, Washington, D.C.

[21] Appl. No.: 894,878

[22] Filed: Aug. 8, 1986

[51] Int. Cl.$^4$ .................... B01J 13/00; C07C 50/18; C07J 9/00
[52] U.S. Cl. .................. 260/376; 252/315.4; 260/369; 260/383; 260/397
[58] Field of Search .............. 252/315.4; 260/376, 260/369, 383, 397

[56] References Cited

U.S. PATENT DOCUMENTS 3,591,607  7/1971  Furst et al. ............... 260/376
3,772,366  11/1973  Uskokovic et al. ......... 260/376

OTHER PUBLICATIONS

Lin et al, "Novel Gelator", Macromolecules 1987, 20, 414–417.
Rudolph et al, "Membrane Stabilization", Cryobiology 22, 367–377 (1985).

Primary Examiner—Matthew A. Thexton
Assistant Examiner—Catherine S. Kilby
Attorney, Agent, or Firm—Saidman, Sterne, Kessler & Goldstein

[57] ABSTRACT

Stable, thermally reversible gels of organic solvents and a gelling agent having the formula $$R_1-(CH_2)_n-CO_2-R_2$$

wherein $R_1$ is an anthracene analogue or substituted anthracene analogue, n is zero or a whole number from 2 to 20, and $R_2$ is cholesteryl and cholestanyl or a derivative of cholesteryl or cholestanyl, processes for producing same, and novel anthracene analogue cholesteryl and cholestanyl esters and derivatives.

18 Claims, 4 Drawing Sheets

THERMALLY REVERSIBLE ORGANIC SOLVENT GELS

This invention was funded by a research grant from the National Science Foundation, Grant No. CHE83-01776. The U.S. Government has certain rights in the invention.

BACKGROUND OF THE INVENTION

1. Field of the Invention

This invention is directed to the discovery that certain cholesteryl and cholestanyl esters of anthracene analogues, and derivatives thereof, in small quantities, produce stable, thermally reversible gels of organic solvents. The invention relates to the process of gelling organic solvents utilizing the anthracene analogue cholesteryl and cholestanyl esters and derivatives, to the gelled organic solvent compositions which are produced by the process, and to novel anthracene analogue cholesteryl and cholestanyl esters and derivatives for producing same.

2. Background of Related Technology

Gelation is one of the common forms of colloidal behavior, with gels having been prepared for many substances. Gelled forms of organic solvents are of particular interest, with attention currently being focused on controlling the flammability of a large variety of organic solvents in order to significantly reduce fire hazard and improve the handling characteristics of the organic solvents. The patent literature is replete with technology directed to gelling agents for organic solvents.

Weissberger et al., U.S. Pat. No. 2,388,887, disclose the use of 2-alkyl-substituted 1,4-dihydroxybenzene compounds as agents for producing stiff gels with liquid aliphatic hydrocarbons and liquid halogenated aliphatic hydrocarbons.

Hill et al., U.S. Pat. No. 2,751,284, disclose "bodying agents" for gelling normally liquid hydrocarbons and other organic liquids. The gelling agents disclosed by Hill et al. are a 2-component composition, the first liquid composition comprising an aluminum alkoxide in toluene or other aromatic hydrocarbon of high solvency power, and the second liquid composition comprising a mixture of a low molecular weight ketone, water, and $C_6$–$C_{18}$ fatty acids, preferably isooctanoic acids.

Kelly et al., U.S. Pat. No. 3,084,033, disclose thickened, normally liquid hydrocarbons which are useful as fuel or the charge in certain devices such as incendiary missiles, flame throwers, rockets, portable cooking stoves, and the like. The Kelly et al. process comprises mixing the normally liquid hydrocarbons with a very small proportion of solid, crystalline polypropylene. Surprisingly, according to Kelly et al., while propylene functions in the disclosed invention, polymers of other olefins, such as polyethylene and polybutenes were found to be completely ineffective. On the other hand, Sarem, U.S. Pat. No. 3,507,635, discloses gelled jet fuels produced by adding polyisobutylene, the resulting gel capable of being fluidized by high speed shearing, the fluidized gel then suitable for pumping to a jet engine as a fluid.

Hiatt et al., U.S. Pat. No. 3,545,946, disclose petroleum distillate fuel compositions in gelled form, said compositions gelled at room temperature and liquid at elevated temperatures of about 55° C. and above. The gelled compositions comprise 75–95 weight percent of a petroleum distillate fuel and from 5 to about 25 weight percent of a paraffinic hydrocarbon gelling agent containing from about 25 to about 35 carbon atoms per molecule and melting the range of about 140° F. to about 155° F.

Jones et al., U.S. Pat. No. 3,692,504, disclose the production of gelled compositions containing gasoline and other normally liquid hydrocarbons such as benzene, toluene, xylenes, kerosene, naphthas, and the like, said compositions gelled by a process comprising dissolving a synthetic elastomer in a normally liquid hydrocarbon and treating the resulting solution with sulfur dioxide in the presence of a suitable catalyst, i.e., typically, nitrates of the alkali metals, peroxides, hydroperoxides, and the like.

Iwama et al., U.S. Pat. No. 3,807,973, disclose gelled hydrocarbon fuels prepared by gelling the hydrocarbon fuel with a fatty acid diethanolamide, diethanolamine, a fatty acid triethanolamine ester, or a triethanolamine. The Iwama compositions purportedly have the advantage that the gelled hydrocarbons are highly stable, have substantially reduced fluidity, and still retain their desirable burning quality as fuels for heating means, reciprocating engines, diesel engines, jet engines, and the like.

Teng et al., U.S. Pat. No. 3,824,085, disclose esters of hydroxypropyl cellulose and hydroxypropyl starch useful as gelling agents for organic solvents, the gelling agents particularly useful in gelling methylene chloride (useful in paint stripping) and ethyl bromide (useful as soil fumigants). The hydroxypropyl cellulose laurate derivative is disclosed as particularly useful as a gelling agent for jet fuel.

Teng et al., U.S. Pat. No. 3,960,514, improved upon the invention of Teng et al. ('085, supra) by providing a gelled jet fuel having incorporated therein hydroxypropyl cellulose laurate and a synergistic additive comprising an elastic, high molecular weight, synthetic polymer.

Tarpley, U.S. Pat. No. 4,156,594, discloses a thixotropic gel fuel composition comprising 5 to about 75 volume percent of a solid carboniferous combustible material suspended in a liquid fuel and about 1 to about 10 weight percent of a substantially completely combustible gelling agent, said combustible gelling agent selected from the group consisting of natural and synthetic gums, resins, modified castor oil polymers, and the like.

Other gelling agents have been used for organic liquids as well. Saito et al., U.S. Pat. No. 3,969,087, disclose the use of a small amount of N-acyl amino acids or derivatives thereof, such as esters, amides, and amine salts of the N-acyl amino acids, as gelling agents for nonpolar organic liquids.

Vaterodt, U.S. Pat. No. 2,719,782, discloses the formation of gels from solvents such as hexane, heptane, octane, terpenes, sesqui-terpenes, benzene, ethyl acetate, and the like, including essential oils for use in the perfume industry. The gelling agent disclosed by Vaterrodt comprised lanosterol, prepared by saponifying wool grease with sodium hydroxide, thereafter removing the lanoline acids as the insoluble calcium salt, and removing the lanolin alcohols by a suitable solvent such as acetone. The lanosterol was obtained from the lanolin alcohol filtrate by precipitation with acetone and methanol. The gelled hydrocarbons of Vaterrodt comprised 8–15% of lanosterol.

Terech, P. et al., *J. Physique* 46: 895–903 (1985) presented the results of a Small Angle Neutron Scattering (SANS) study of a gel formed by a dilute solution (less than one weight percent solution) of a paramagnetic modified steroid, 3-beta-hydroxy-17,17-dipropenyl-17a-aza-D-homoandrostanyl-17a-oxy in cyclohexane.

Tachibana, T. et al., *Bull. Chem. Soc. Jpn.* 53: 1714–1719 (1980), describe optically active 12-hydroxyoctadecanoic acids which form thermally reversible gels with aromatic solvents or carbon tetrachloride. The authors further discussed the work of Samulski, E. T. et al., "Liquid Crystals and Plastic Crystals," Ed. by G. W. Gray and P. A. Winsor, Ellis Horwood, Chichester, pp. 175–198 (1974), who purportedly described a cholesteric mesophase formed by synthetic polypeptides in organic solvents.

However, in spite of the substantial amount of work devoted to developing gelled organic solvents, a need has continued to exist for highly stable, thermally reversible, gelled organic solvents, particularly for use as fuels, wherein the gelling agent is present in a small percentage and does not function as an impurity in the combustion process.

SUMMARY OF THE INVENTION

In the present invention, normally liquid organic solvents are converted into stable, thermally reversible gels by the addition of 0.1–5% preferably 0.1 to 2% or less of a gelling agent having the general formula (I):

$$R_1-(CH_2)_n-CO_2-R_2 \qquad (I)$$

wherein n is zero or a whole number between 2 and 20, $R_1$ is an anthracene analogue, and $R_2$ is selected from the group consisting of cholesteryl, cholestanyl and their derivatives.

DESCRIPTION OF THE PREFERRED EMBODIMENTS

Figure 1:
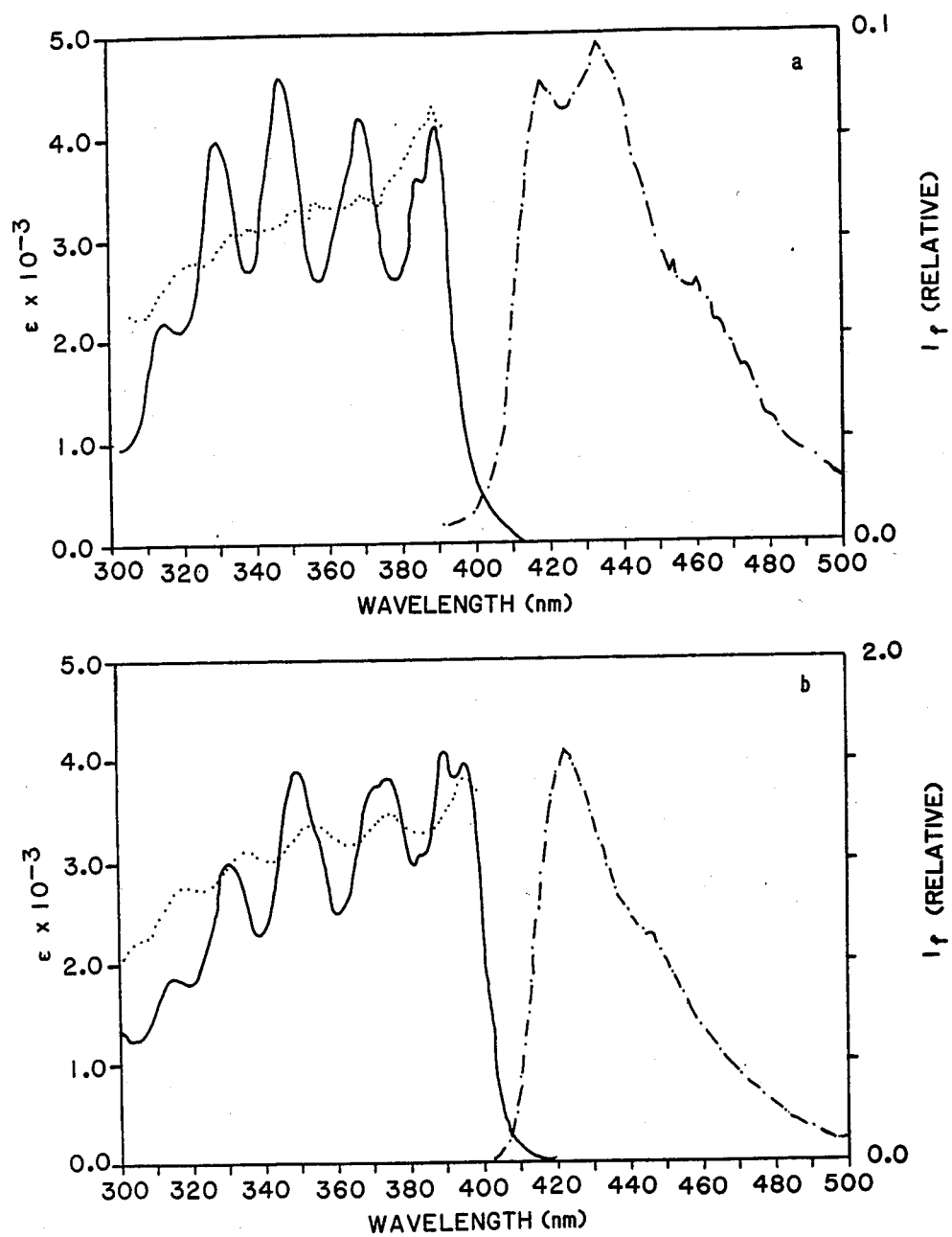
FIG. 1 is a graph demonstrating representative plots of emission intensity plotted against wave length for a 0.72% solution of CAB in n-dodecane. Isotropic (a; 67° C.) and gel (b; 25° C.) absorption (———), fluorescence ($\lambda$exit., 346 nm; - --- -), and excitation ($\lambda$emiss., 433 nm (a) and 422 nm (b); . . . ) spectra are shown. The sample was not degassed. The fluorescence intensities between (a) and (b) are shown to observed scale.

According to the present invention, gels may be prepared by homogeneously admixing the organic solvent with an effective amount of a compound having the general formula (I) as described above.

By the term "organic solvent(s)" is included non-polar organic liquids including petroleum hydrocarbons such as gasoline, naphthas, kerosene, gas oil, heavy oil, and crude oil; lubricating oils such as spindle oil and turbine oil, liquid paraffin, pure hydrocarbons such as xylene, alkanes having one to thirty carbon atoms, i.e. hexane, heptane, octane, decane, tetradecane and hexadecane; cyclohexanes such as decalin and cyclohexane; alkenes having one to thirty carbon atoms such as 1-tetradecene and 1,3-penta diene; alkanols having one to twenty carbon atoms, such as 1-propanol, 1-octanol, 1-dodecanol, and 4-heptanol; benzyl alcohol; esters such as n-pentylacetate, butyl acetate, amyl acetate, diethyl phthalate, dibutyl phthalate, dioctyl phthalate, diethyl sebacate and dioctyl sebacate; alkanoic acids such as nonanoic acid; aldehydes such as anisaldehyde and heptanal; phosphoric esters, such as tributyl phosphate and tricresyl phosphate; amines such as n-butylamine, benzylamine, N-methylamine, and alpha-methylbenzylamine; normally liquid polyoxyalkylene monoalkyl ethers such as polyoxyethylenemonolauryl ether containing four to six oxyethylene units, polyoxypropylene mono $C_4$–$C_{12}$ alkyl ether containing 10–50 oxypropylene units; normally liquid polyoxypropylenemonolauryl ether; normally liquid polyoxyalkylene glycol fatty acid esters such as polyoxyethylene glycol lauric or oleic acid esters containing four to six oxyalkylene units; fatty oils such as corn oil, soybean oil, olive oil, rape seed oil, cotton seed oil, sardine oil, herring oil, and whale oil; silicone oil, and mixtures thereof.

In the general formula (I) above, $R_1$ is an anthracene analogue. By the term "anthracene analogue" is intended moieties having a structural formula selected from the group consisting of

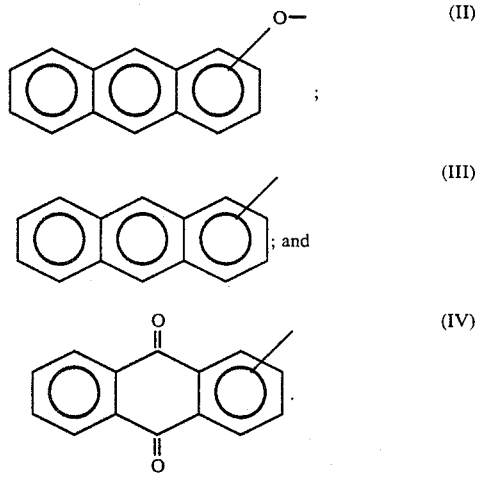

Additionally, one or more of the fused rings may be substituted in one or more positions with a halogen, a $C_1$–$C_4$ alkyl, a $C_1$–$C_4$ alkoxy, a phenyl, or a $C_1$–$C_4$ alkyl substituted phenyl group. The substitution of the anthracene analogue with one or more of the above groups is hereinafter referred to as "a substituted anthracene analogue."

Additionally, in the general formula (I) above, n is zero or a whole number between 2 and 20, preferably between 2 and 8, more preferably between 2 and 5.

In the present invention, $R_2$ is a moiety selected from the group consisting of cholesteryl and cholestanyl and their derivatives. By "cholesteryl" is intended a moiety having the formula (V):

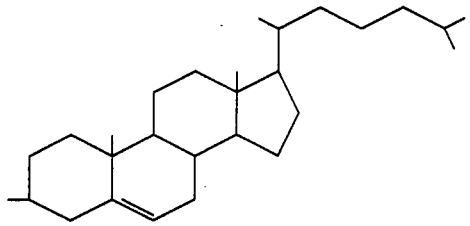

By "cholestanyl" is intended a moiety having the formula (VI):

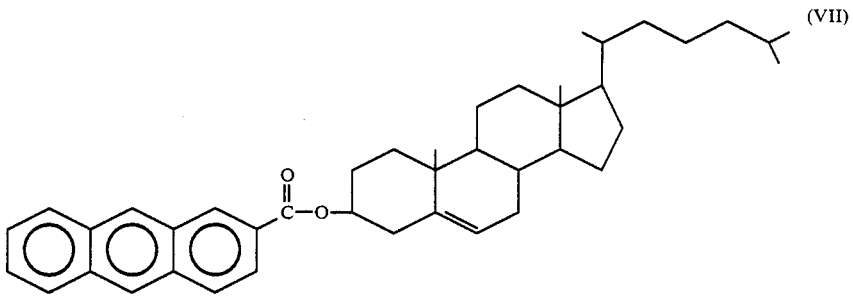

By "derivative" is intended the parent molecular skeletons of cholesteryl and cholestanyl in which one or more hydrogen atoms have been removed or have been replaced by other atoms or groups of atoms (e.g., —halogen, —$NH_2$, =O, —OH, —SH, —$CO_2H$, —CHO, —$R_3$ [where $R_3$ is a simple or complex group of atoms for which the atom linked to the parent molecular skeleton is carbon], —$CO_2R_3$, —$SR_3$, —$OR_3$, —$NHR_3$, —$N(R_3)_2$, and the like).

The preferred gelling agents of the present invention include the following compounds:

A. Cholesteryl anthracene-2-carboxylate(CA-2), said compound having the formula (VII):

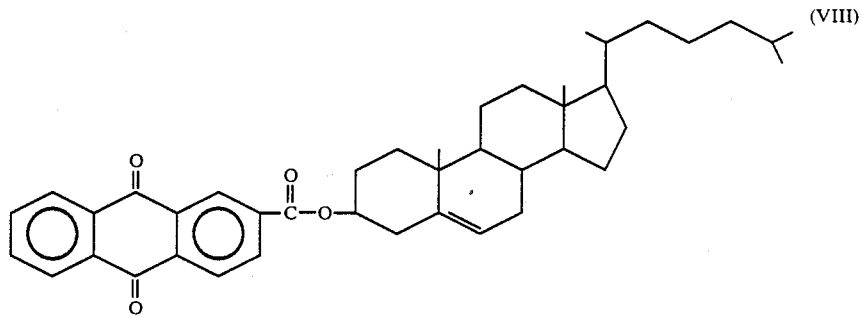

B. Cholesteryl anthraquinone-2-carboxylate(CAQ) said compound having the formula (VIII):

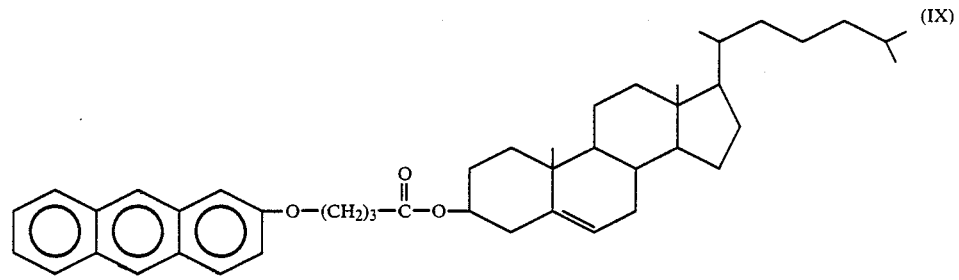

C. Cholesteryl 4-(2-anthryloxy)butanoate (CAB), said compound having the formula (IX):

D. Cholesteryl 5-(2-anthryloxy)pentanoate(CAP), said compound having the formula (X):

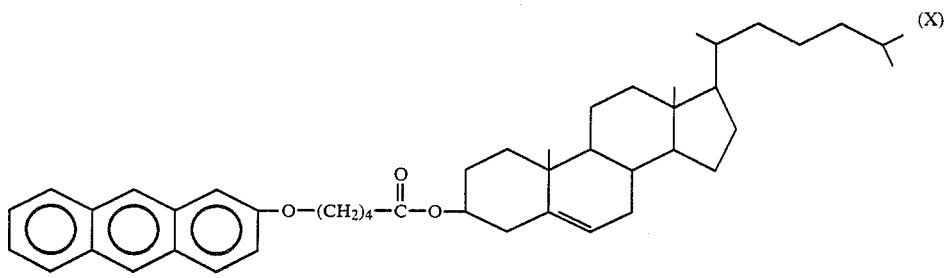

and E. six-ketocholestanyl 4-(2-anthryloxy)butanoate(-KAB), said compound having the formula (XI):

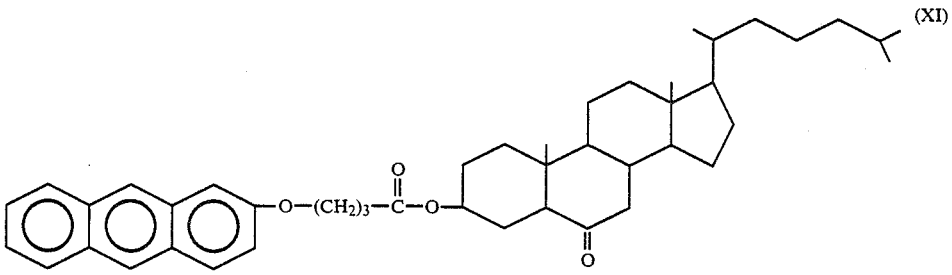

By the term "an effective amount of" is intended that amount sufficient to effect the desired gelling of the organic solvent. Typically, the gelling agent is used in an amount of 0.1–5%, preferably 0.1–2%, or less. As is understood by those skilled in the art, the lower the amount of gelling agent the more desirable the composition inasmuch as the gelling agent demonstrates chemical and physical properties which differ from the end-use properties of the gelled organic solvents. Accordingly, it is desirable to minimize the amount of gelling agent required.

The gels of the present invention may be prepared simply by homogeneously admixing a gelling agent having the above formula (I) with an organic solvent under conditions sufficient to effect dissolution and allowing the solution to gel. Homogeneous admixing of the reactants may be conducted at temperatures ranging from room temperature to the boiling point of the organic solvent. The gelling agent may be added in the form of powder particles or as solutions dissolved in a suitable solvent, typically the solvent being gelled, or other suitable solvent such as acetone, methanol, or ethanol. The gels of the present invention may also be formed by dissolving the gelling agent in the organic liquid at elevated temperatures, and thereafter cooling the resulting solution to a lower temperature, whereby gel formation occurs while standing.

According to the present invention, the gelling agent may be employed generally in the range of about 0.05% to 20% by weight based upon the organic solvent to be gelled, preferably 0.1 to 1.5% or less. The firmness of the resulting gel may be optionally varied depending on the kind and amount of gelling agent added. A suitable amount of gelling agent may be determined experimentally and will vary with the desired physical property of the gel and other components therein. When preparing gels in accordance with the process of this invention, the requisite amount of gelling agent is admixed with the organic solvent and the materials are blended, under existing conditions of temperature and pressure. However, different temperatures and pressures may be utilized in the mixing process where, for example, loss of vapors, in the case of a low-boiling hydrocarbon, is to be avoided or easier mixing, in the case of higher-boiling hydrocarbons is to be obtained.

The components are mixed by any means such as stirring, shaking, or passing the mixture through a homogenizer to produce a homogeneous composition. Regardless of the method of blending, gels are produced as a result of obtaining an intimate dispersion of the gelling agent in the organic solvent.

The normally liquid organic solvent of the present invention, once gelled, varies in viscosity from a thin, pourable type to a shape retaining gel. The resulting gels are highly cohesive, stable in storage for variable periods (depending upon the gelling agent, its concentration, the solvent, and the temperature of storage), thermally reversible, and are sheerstress thinnable.

The practice of the present invention is particularly well suited for use in the fuel industry. In the practical use of fuel, it is frequently desirable to store fuel in a solid form. This is especially true in the case of aviation jet fuel. The rupturing of fuel tanks in jet aircraft in crashes during landing and takeoff and the resulting spreading of the highly flammable fuel is a problem of substanial proportions. Further, fuel vaporized easily and the fuel vapors are readily ignited by hot engine parts or sparks from metal impact. On the contrary, when fuels are gelled, the degree of vaporization and the extent to which the fuel is scattered upon impact are substantially decreased, with concomitant decrease in the danger of rapidly spreading fire or explosion.

Gelling agents for organic liquids are also useful for facilitating the removal or recovery as a result of unintentional spills. In like manner, gelling agents may be added to tanks which have developed leaks or holes, thereby preventing further loss of the tank contents.

Additionally, the gelling agents may be used in the preparation of paints, inks, greases, oil-type cosmetics, napalm-type incendiaries, display devices (such as electro-optical switching screens, television screens, etc.), and films (such as X-ray and visible photographic films, heat sensitive films, information storage devices, and the like).

The gelling agents of this invention are particularly advantageous in that, as carbohydrates, the gelling agents provide no residue problem in fuels.

Having now generally described the invention, a further understanding may be obtained by reference to certain specific examples which are provided herein for purposes of illustration only and are not intended to be limiting unless otherwise specified.

EXAMPLE I

Beta-Cholesteryl anthracene-2-carboxylate (CA-2)

A mixture of 0.1 g anthracene-2-carboxylic acid and 0.4 ml oxalyl chloride in 50 ml dry benzene were stirred and refluxed (bath temperature ca. 50°–80° C.) under a dry atmosphere for 16 hours. A yellow solid was obtained after removal of solvent and excess oxalyl chloride by vacuum distillation. The crude acid chloride was washed quickly with benzene (2×25 ml) and was mixed with a solution of 0.17 g beta-cholesteryl in 20 ml benzene containing a trace of pyridine. After 3 hours of stirring and refluxing (bath temperature ca. 50°–70° C.), 50 ml of water were added. The mixture was extracted with chloroform (3×25 ml). The organic layer was washed twice with 25 ml of 10% aqueous sodium hydroxide and twice with 25 ml water. A yellow solid, obtained after evaporating the liquid on a rotary evaporator, was recrystallized twice from tert-amyl alcohol to yield 0.11 g (41%) of needle crystals, mp. ca. 225° C. CA-2 showed a cholesteric liquid-crystalline phase: 220°–225°±5° C. $^1$H NMR (CDCl$_3$/TMS): δ 8.57 (1H, s, ArH), 8.46 (1H, s, ArH) 7.90–8.16 (3H, m, ArH), 7.40–7.62 (4H, m, ArH), 5.46 (1H, d, alkenyl), 5.11–4.68 (1H, m, oxycyclohexyl), 0.70–2.64 (43H, m, cholesteryl moiety). IR (KBr) 1710, 1270, 1235 cm$^{-1}$.

EXAMPLE II

Gelling procedure: a mixture of 2.8% (by weight) of CA-2 in n-dodecane was heated until it became homogeneous and was then cooled to ambient temperature. Cooling to ambient temperature led to gel formation.

EXAMPLE III

Beta-Cholesteryl anthraquinone-2-carboxylate (CAQ)

A mixture of 0.3 g anthraquinone-2-carboxylic acid and 0.9 ml oxalyl chloride in 25 ml dry benzene was stirred and heated (bath temperature ca. 40°–50° C.) in a dry atmosphere for 1 hour. Benzene and excess oxalyl chloride were removed by vacuum distillation. The crude acid chloride, a yellow solid residue, was washed rapidly with benzene (2×25 ml) and was stirred for 16 hours at ambient temperature under a dry atmosphere with 0.46 g of beta-cholesterol in 20 ml of benzene and 2 drops of pyridine. A yellow solid, obtained after benzene was evaporated on a rotary evaporator, was crystallized twice from chloroform/methanol to yield 0.55 g (75%), mp. 229° C. CAQ showed a liquid-crystalline phase: 170°–229° C. $^1$H NMR (CDCl$_3$/TMS): δ 8.87, 8.23–8.40, 7.72–7.80 (7H, m, ArH), 5.4 (1H, d, Alkenyl), 4.8–5.0 (1H, m, oxycyclohexyl), 0.6–2.6 (43H, m, cholesteryl).

EXAMPLE IV

Gelling procedure: a mixture of 2.62% (by weight) of CAQ in 4-heptanol was heated until the solid dissolved. Cooling to ambient temperature led to gel formation.

EXAMPLE V

Beta-Cholesteryl 4-(2-anthryloxy)butanoate (CAB)

The synthesis of CAB is described starting from its individual intermediates.

(a) 2-(4-methoxybenzoyl)benzoic acid

Anhydrous aluminum chloride (140 g) was added at ambient temperature to a vigorously stirred mixture of 148 g of phthalic anhydride, 250 ml anisole, and 250 ml carbon disulfide. After 2.5 hours, the solution was hydrolyzed with ice water and the organic solvents were removed by steam distillation. A gray solid which precipitated when the residual solution cooled to room temperature was separated from the liquid by decantation and dissolved in ca. 1 L chloroform. Rotary evaporation of the chloroform left 107 g (42%) of white solid which was recrystallized from acetic acid/water: mp. 142°–144.5° C. (lit.* mp. 122°–123.5° C.). IR (KBr): 1686, 1660 (two different carbonyls), 1550–1600, 1420–1370, 1280, 1255, 1170, 1150, 1015, 850, 800, 755 cm$^{-1}$.

*Iwata, M. et al., *Bull. Chem. Soc. Jpn.* 47:1687 (1974).

(b) 2-(4-methoxybenzyl)benzoic acid 2-(4-Methoxybenzoyl)benzoic acid (30 g), 300 ml of 20% ammonium hydroxide, and 30 ml of 20% ammonium hydroxide containing 2.5 g cupric sulfate were added together and stirred and heated to gentle reflux. Then, 75 g of zinc powder were added slowly. After 24 hours of stirring at ca. 95°–100° C., the mixture was cooled, filtered, and acidified with 1 L of 10% hydrochloric acid to give a white precipitate. The white solid was collected and crystallized from 50% aqueous ethanol to yield 27 g (95%) of white crystals: mp. 113.5°–115° C. (lit.* mp 117°–118° C.). IR (KBr): 1650–1700 (carbonyl), 1610, 1500, 1455, 1445, 1400, 1320–1230, 1175, 1145, 1100, 1070, 1040, 940–900, 850, 830, 810, 770, 760, 750 cm$^{-1}$.

*Iwata, M. et al., supra.

(c) 2-methoxy-9-anthrone 2-(4-Methoxybenzyl)benzoic acid (20 g) was dissolved in 94 ml ice-cold conc. sulfuric acid. After 2 hours stirring in an ice bath (ca. 0.5° C.), the solution was poured into ca. 700 ml of ice water and a yellow precipitate formed. Extraction of the aqueous mixture with methylene chloride (2×100 ml) followed by removal of solvent on an rotary evaporator yielded 11 g (59%) of a yellow solid, mp. 94.5°–97.5° C. (lit.* mp 96°–97.5° C.

*Iwata, M. et al., supra.

(d) 2-methoxyanthracene

A well-stirred mixture of 20 g zinc dust, 2 ml Fehling I solution, and 120 ml of water was added to a suspension of 8 g 2-methoxy-9-anthrone and 200 ml of 10% aqueous sodium hydroxide. The mixture was refluxed for 30 minutes and filtered hot to give a gray solid. The solid was heated on a steam bath and swirled vigorously while 120 ml of conc. hydrochloric acid were added drop by drop over a 40 min. period. A crude, slightly yellow solid was collected on a Buchner funnel, washed with 100 ml water and 50 ml methanol, and then crystallized from benzene twice to give 6.4 g (86%) of plate-like crystals: mp. 182.5°–183.5° C. (lit.* mp 163–165). IR (KBr): 1635, 1480, 1465, 1435, 1345, 1220–1175, 1300–1270, 1025, 950, 880, 800, 740 cm$^{-1}$. $^1$H NMR (CDCl$_3$/TMS): δ8.3 (1 H, s, anthrancenyl meso proton), 8.2 ( H, s, anthracenyl meso proton, 7.75–8.05 (3 H, m, oxyanthracenyl protons), 7.05–7.50 (4 H, m, oxyanthracenyl protons), 3.95 (3 H, s, ArOCH$_3$).

*Iwata, M. et al., supra.

(e) 2-hydroxyanthracene

A solution of 2 g of 2-methoxyanthracene and 25 ml methylene chloride were stirred and chilled at −70° C. (acetone/dry-ice bath) under a dry atmosphere. A solution of 60 ml of methylene chloride and 11 ml of 1N boron tribromide in methylene chloride was added slowly through a compensating addition funnel. The mixture was then allowed to warm slowly to ambient temperature under a dry atmosphere. After 24 hours, 20 ml of water were added and the mixture was extracted with ether (4×25 ml). A brown solid, 1.7 g (92%), decomp. ca. 200° C. (lit.** decomp. 200° C.) was obtained after ether evaporation and drying under vacuum for 16 hours. IR (KBr): 3540–3460, 3460–3100 (—OH), 1630, 1480, 1460, 1410, 1380, 1320, 1280–1270, 1200–1170, 950, 880, 800, 735 cm$^{-1}$. $^1$H NMR (CD$_3$COCD$_3$/TMS): δ8.3, 8.44, 8.8; 8.13–7.8; 7.15–7.52 (ArH).

**(a) Buckingham, J. E., *Dictionary of Organic Compounds*, 5th ed., Chapman and Hall: New York, 1982, Vol. 1, p. 390;
(b) Logodzinski, K., *Justus Liebigs Ann. Chem.* 342:59 (1905).

(f) Ethyl 4-(2-anthryloxy)butanoate

A 30 ml solution of dimethylformamide containing 1.01 g of 2-hydroxyanthracene was added, with stirring, to 20 ml dimethylformamide containing ca. 0.125 g of sodium hydride (from 0.25 g of 50% oil-dispersion, washed thrice with 10 ml pentane). After hydrogen evolution ceased, 0.7 ml of ethyl 4-bromobutanoate was added to the solution. After stirring for 48 hours under a dry atmosphere, 50 ml of water were added to the reaction mixture. It was extracted with methylene chloride (5×50 ml), and the combined organic layers were washed with 50 ml of 10% aqueous sodium carbonate and water (4×50 ml), and then dried over anhydrous magnesium sulfate. After evaporating the solvent, the crude product was crystallized three times from 95% ethanol to yield 0.8 g (50%) of crystals, mp. 128.5°–129° C. IR (KBr): 1735 (ester carbonyl), 1625, 1455, 1430, 1390, 1380, 1300–1270, 1200–1180, 1080, 1050, 1010, 880, 800, 740 cm$^{-1}$. $^1$H NMR (CDCl$_3$/TMS): δ8.35 (1 H, s, anthracenyl meso proton), 8.15 (1 H, s, anthracenyl meso proton), 7.7–8.0 (3 H, m, oxyanthracenyl protons), 7.0–7.5 (4 H, m, oxyanthracenyl protons), 4.0–4.3 (4 H, m, MeC$\underline{H}_2$OC=O and ArOC$\underline{H}_2$), 2.0–2.7 (4 H, m, —C$\underline{H}_2$C$\underline{H}_2$COO), 1.25 (3 H, t, J=7.2 Hz, C$\underline{H}_3$).

(g) 4-(2-Anthryloxy)butanoic acid

Ethyl 4-(2-anthryloxy)butanoate (0.15 g) was dissolved in 10 ml of hot 95% ethanol, and the solution was added to 20 ml aqueous 5% NaOH. The turbid mixture was boiled so as to allow the ethanol to evaporate slowly. When the vapors no longer contained the smell of alcohol, ca. 500 ml water were added. The resulting clear solution was acidified with dilute hydrochloric acid until a precipitate formed. The precipitate was extracted with chloroform (3×50 ml) and the combined extracts were evaporated (rotary evaporator) to yield a yellow solid. It was recrystallized from toluene to yield 0.09 g (66%) of yellow needle crystals, mp. 190°–193° C. IR (KBr) 2500–3000, 1705 (acid carbonyl), 1630, 1470, 1455, 1430, 1410, 1300–1245, 1200–1180, 1045–1020, 880, 800, 780, 735 cm$^{-1}$.

(h) Beta-Cholesteryl 4-(2-anthryloxy)butanoate (CAB)

A mixture of 4-(2-anthryloxy)butanoic acid (0.17 g), 10 ml dry benzene, and 0.5 ml oxalyl chloride was stirred and heated (bath temperature ca. 50°–60° C.) under a dry atmosphere for ca. 2.5 hours. Benzene and excess oxalyl chloride were distilled under vacuum. The yellow residue was mixed with a solution of 25 ml benzene, 0.244 g beta-cholesterol, and a trace of pyridine. After ca. 16 hours of stirring under a dry atmosphere at ca. 50° C., the solvent was evaporated (rotary evaporator) and the solid was crystallized three times from tert-amyl alcohol and three times from methanol/chloroform. The resulting white crystals, 0.22 g (79%), mp. 204°–206° C., showed a monotropic cholesteric liquid-crystalline phase (196°–160° C.). IR (KBr): 1735 (ester), 1630, 1455, 1410, 1275, 1280–1245, 1170, 1050, 1020, 1000, 880, 800, 740 cm$^{-1}$. $^1$H NMR (CDCl$_3$/TMS): δ8.32 (1 H, s, anthracenyl meso proton), 8.24 (1 H, s, anthracenyl meso proton), 7.83–8.00 (3 H, m, oxyanthracenyl protons) 7.35–7.46 (2 H, m, oxyanthracenyl protons), 7.10–7.24 (2 H, m, oxyanthracenyl protons), 5.36 (1 H, s, alkenyl), 4.60–4.70 (1 H, m, oxycyclohexyl), 4.17 (2 H, t, J=5.86 Hz, ArOC$\underline{H}_2$), 2.56 (2 H, t, J=6.88 Hz, C$\underline{H}_2$COO), 0.67, 0.82, 0.90–2.2 (46 H, m, methylene and cholesteryl protons).

EXAMPLE VI

Gelling procedure: a mixture of 1.51% (by weight) of CAB in heptanal was heated until it became a solution. Gel formed as the solution cooled to room temperature.

EXAMPLE VII

Beta-Cholesteryl 5-(2-anthryloxy)pentanoate (CAP)

A mixture of 5-(2-anthryloxy)pentanoic acid (0.254 g), 15 ml dry benzene, and 6 ml oxalyl chloride was stirred and heated under a dry atmosphere for 2 hours. Benzene and excess oxalyl chloride were distilled under vacuum. The yellow residue was then mixed with a solution of 25 ml benzene, 0.389 g of beyta-cholesterol, and a trace of pyridine. After ca. 16 hours of stirring under a dry atmosphere at ambient temperature, the solvent was evaporated and the residue was crystallized three times from methanol/chloroform to yield 0.42 g (63%), mp. 129°–131° C. $^1$H NMR (CDCl$_3$/TMS): δ8.32 (1 H, s, anthracenyl meso proton), 8.24 (1 H, s, anthracenyl meso proton), 7.83–8.00 (3 H, m, oxyanthracenyl protons) 7.35–7.46 (2 H, m, oxyanthracenyl protons), 7.10–7.24 (2 H, m, oxyanthracenyl protons), 5.36 (1 H, s, alkenyl), 4.60–4.70 (1 H, m, oxycyclohexyl), 4.14 (2 H, t, J=6.05 Hz, ArOC$\underline{H}_2$), 2.56 (2 H, t, J=6.88 Hz, C$\underline{H}_2$COO) 0.67–2.4 (48 H, m, methylenes and cholesteryl protons).

EXAMPLE VIII

Gelling procedure: a mixture of 1.31% (by weight) CAP in n-dodecane or 1.29% CAP in 4-heptanol was heated until all solid dissolved. Gel formed as the solution cooled to room temperature.

EXAMPLE IX

Beta-6-Ketocholestanyl 4-(2-anthryloxy)butanoate (KAB

KAB was synthesized by esterification of 4-(2-anthryloxy)-butanoyl chloride (from 0.094 g of 4-(2-anthryloxy)butanoic acid and 4 ml oxalyl chloride in 50 ml dry benzene) with 0.142 g 3-beta-hydroxy-6-cholestanone. The crude product was crystallized three times from methanol/chloroform to yield 0.17 g (76%), mp. 199°–201° C. $^1$H NMR (CDCl$_3$/TMS): 8.2–8.35 (2 H, m, anthracenyl meso protons), 7.80–8.00 (3 H, m, oxyanthracenyl), 7.35–7.45 (2 H, m, oxyanthracenyl protons), 7.10–7.20 (2 H, m, oxyanthracenyl protons), 4.65–4.80 (1 H, m, oxycyclohexyl in 6-ketocholestanyl moiety), 4.15 (2 H, t, J=4.7 Hz, ArCH2), 2.74 (2 H, t, CH2COO), 2.55, 2.4–2.15, 2.1–1.0, 0.91–0.84, 0.75, 0.64 (47 H, m, ketocholestanyl moiety and methylene).

EXAMPLE X

Gelling procedure: a mixture of 1.21% (by weight) KAB in n-dodecane or 1.21% of KAB in n-octanol was heated until all solid dissolved. Gel formed as the solution cooled to room temperature.

EXAMPLE XI

In a typical procedure, a mixture of CAB (ca. 1% by weight) and a solvent is heated until a solution obtains. Cooling to ambient temperatures results in gel formation as witnessed visually by a rapid increase in viscosity and a decrease in translucence. Gel formation was followed quantitatively by ultraviolet absorption spectroscopy or, more conveniently, by fluorescence from the anthracenyl lumophore. A large (ca. 10 fold) increase in emission intensity and a significant change in emission spectral shape are observed as the gel forms. No band ascribable to a CAB excimer (Birks, J. B., "Photophysics of Aromatic Molecules," Wiley Interscience: LONDON, chapter 7 (1970)) was detected in either the isotropic or gel phase. Representative spectra of 0.72% CAB in n-dodecane are presented in FIG. 1. The change in the wavelength of emission maximum is not thermally induced since emission spectra of both high temperature and very dilute ambient temperture solutions of CAB (which do not gel) exhibit λmax 417 and 432 nm. The gel maximum is near 422 nm.

The excitation spectra for the same solution used in FIG. 1 showed maxima which correspond to the vibronic progression of the anthracenyl chromophore. In the isotropic phase, the 0—0 and 0—1 bands of the $^1L_a$ absorption (Mason, S. F. et al., Chem. Phys. Lett. 21, 406 (1973)) appear at 390 and 370 nm, respectively. The excitation and absorption spectra in the gel phase are more complex. The absorption spectra show new bands at 396 and 376 nm in addition to those observed in the isotropic spectrum. The excitation spectra of the gel display the 396 and 376 nm bands much more prominently than the 390 and 370 nm bands. Order and proximity among CAB molecules appear necessary to observe the new bands: 0.81% of CAB in a 30/70 (w/w) cholesteryl chloride/cholesteryl nonanoate mixture at 40° C. (cholesteric liquid-crystalline phase) and at >80° C. (isotropic phase) gave absorption spectra in which the 396 and 376 nm bands were absent. From the above data, the lack of excimer emission and by analogy to studies with anthracene (Chandross, E. A. J. Chem. Phys. 43: 4175 (1965); Ferguson, J. et al., Aust. J. Chem. 26: 91,103 (1973); Chandross, E. A. et al., J. Chem. Phys. 45: 3546 (1966); Chandross, E. A. et al. Ibid. 45: 3554 (1966); Martinaud, M., "These de Docteur d'Etat Es-Sciences," University of Bordeaux I, Talence, France (1975); Martinaud, M. et al., J. Phys. Chem. 82: 1497 (1978)), the new bands are ascribed to vibronic coupling of aggregated anthracenes (stacked but with their long molecular axes nonparallel).

Figure 2:
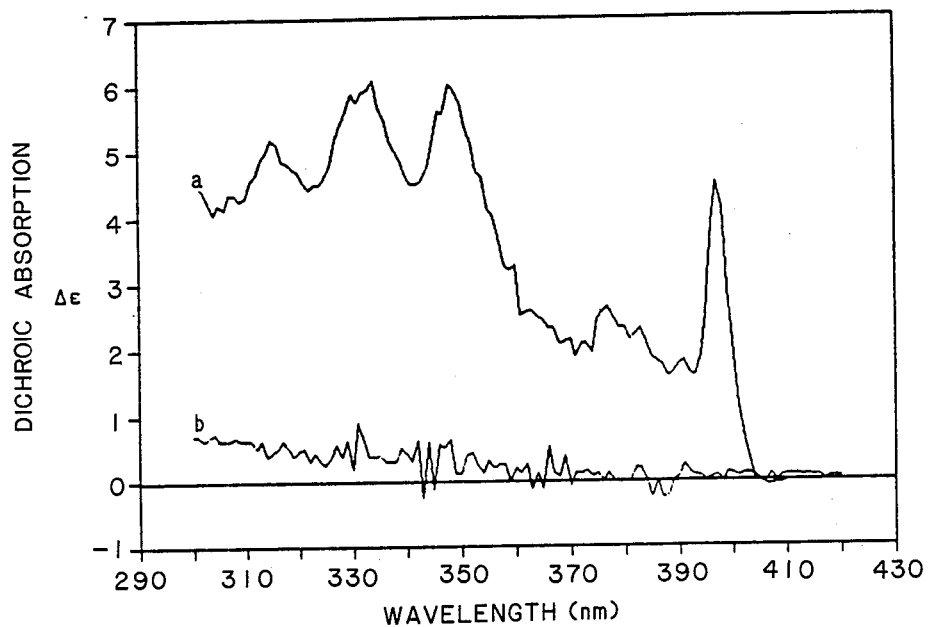
FIG. 2 is a graph plotting the magnitude of dichroic absorbtion against wave length of 0.72% CAB in n-dodecane in the isotropic (a; 63° C.) and gel (b; 18° C.) phases.

Others (Anderson, V. C. et al., J. Am. Chem. Soc. 106: 6628 (1984); Saeva, F. D., Pure Appl. Chem. 38: 25 (1974) and references cited therein; Saeva, F. D., In "Liquid Crystals. The Fourth State of Matter" Saeva, F. D., Ed.; Marcel-Dekker: New York, chap. 6 (1979)) have observed intense circular dichroism spectra of quest molecules in cholesteric liquid crystals. The induced dichroism has been related to the helical arrangement of the solvent matrix. The presence of strong circular dichroism in CAB gels is further evidence for aggregation and for a helical stacking of anthracenyl units. As seen in FIG. 2, the magnitude of dichroic absorption, like emission, increases enormously upon gellation. The bands at 396 and 376 nm are present with the former being the more intense.

Attempts to detect helicity and crystal-like order of CAB molecules in a gel with n-dodecane by x-ray diffraction (Angles from 3° to 30° were scanned on a Picker diffractometer using Mo $K_\alpha$ (λ=0.7107 A) radiation.) were unsuccessful. Only a broad hump centered near a Bragg distance of 5–6 A (and ascribable to hydrocarbon-hydrocarbon chain separations) were recorded. The hump was not shifted in the isotropic phase.

The gel structure is detectable by optical microscopy performed with polarized light. The extent of gel structure depends upon CAB concentration. Branching of the fan-like structures and the overlap between them increase with the weight precent of CAB. In some gels viewed through crossed polarizers, a faint focal conic texture (Maltese crosses reminiscent of patterns observed with liquid crystals (Demus, D. et al., Mol. Phys. 27: 377 (1974)) was discernible. These are samples in which the gel had been formed between microslides and, therefore, may have been aligned.

Some manifestations of the gel structure should be and are found in the photochemistry of CAB. Irradiations (>300 nm) of CAB under a variety of conditions results in formation of three photodimers which are linked at the 9 and 10 positions of the anthracenyl groups. Four photodimers of this type are conceivable. Although the stereochemical assignments of these dimers have not been completed, it is clear from their distributions (Table 1 below) that the photochemistry of the gel phase is very similar to that of the neat liquid-crystalline and isotropic phases. Both of these differ especially from the A/C dimer ratio observed in isotropic toluene solutions. The fact that the (A+B)/C ratios are nearly constant except for the toluene solution may be fortuitous or indicative of similar alignment of CAB molecules in the gel, liquid-crystalline, and neat isotropic phases. Comparisons among these data suffer several limitations (differing temperatures, concentrations, and percents of CAB conversion). Yet, the fact that photodimers arise from very short-lived singlet states (<15 ns) (Ferguson, J. et al., Mol. Phys. 27: 377 (1974); Marcondes, M. E. R. et al., J. Am. Chem. Soc. 97: 4485 (1975)) requires that the dimer distributions reflect in some ways the orientations of CAB molecules in the unirradiated bulk. To the extent that this is so, the photodimers indicate that the stacking of CAB in the gel and in the liquid crystal are not very different. In fact, all of the evidence is consistent with gelled CAB being arranged in helically stacked threads.

TABLE 1

| DISTRIBUTION OF PHOTODIMERS FROM CAB | | | | | |
|---|---|---|---|---|---|
| | | Temp. | Dimers (%) | | |
| Sample | Phase | (°C.) | A | B | C |
| 1.12% CAB-dodecane | gel | 26.0 | 29 | 19 | 53 |
| 1.47% CAB-dodecane | gel | 25.5 | 28 | 16 | 56 |
| 1.47% CAB/toluene | isotropic | 25.5 | 37 | 17 | 46 |
| CAB | liquid-crystalline | 184.4 | 33 | 12 | 56 |
| CAB | liquid-crystalline | 183.5 | 33 | 13 | 55 |
| CAB | liquid-crystalline | 178.0 | 34 | 14 | 53 |
| CAB | isotropic | 204.4 | 31 | 20 | 50 |

Figure 3:
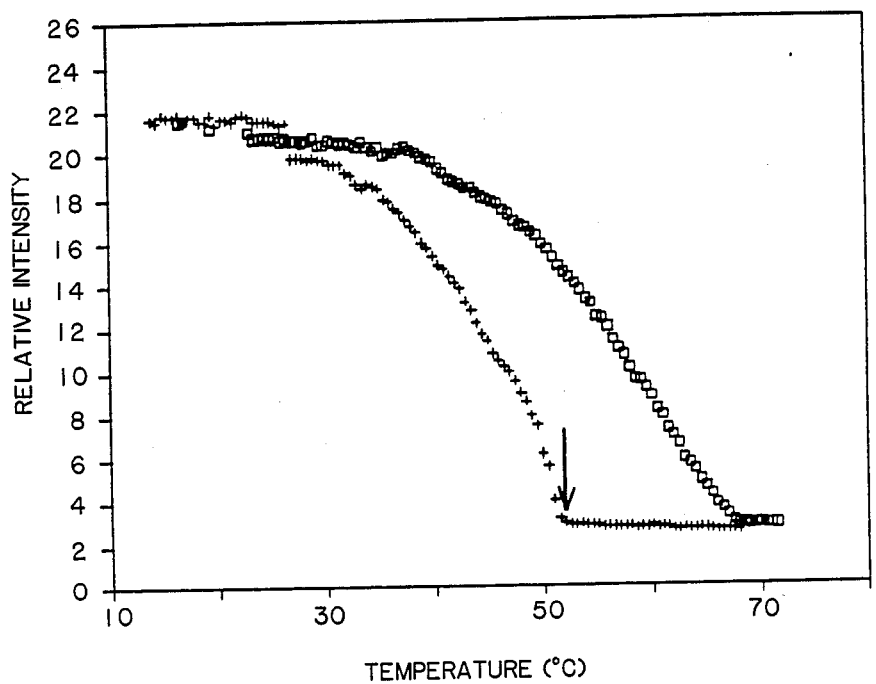
FIG. 3 is a graph plotting fluorescence intensity at 422 nm ($\lambda$exit., 355 nm) of 1.43% CAB in n-dodecane versus temperature. Cooling (+) and heating (□) cycles are shown. The arrow indicates the temperature at which gellation is taken to commence.

The gellation point is somewhat broad and subjective. It is defined for the purposes of this invention to be the temperature at which the onset of emission intensity increase is observed during a cooling cycle of an isotropic solution. It appears to be independent of cooling rate, at least for n-alkane solutions. A representative plot of 1.43% of CAB in n-dodecane versus temperatures is presented in FIG. 3.

Figure 4:
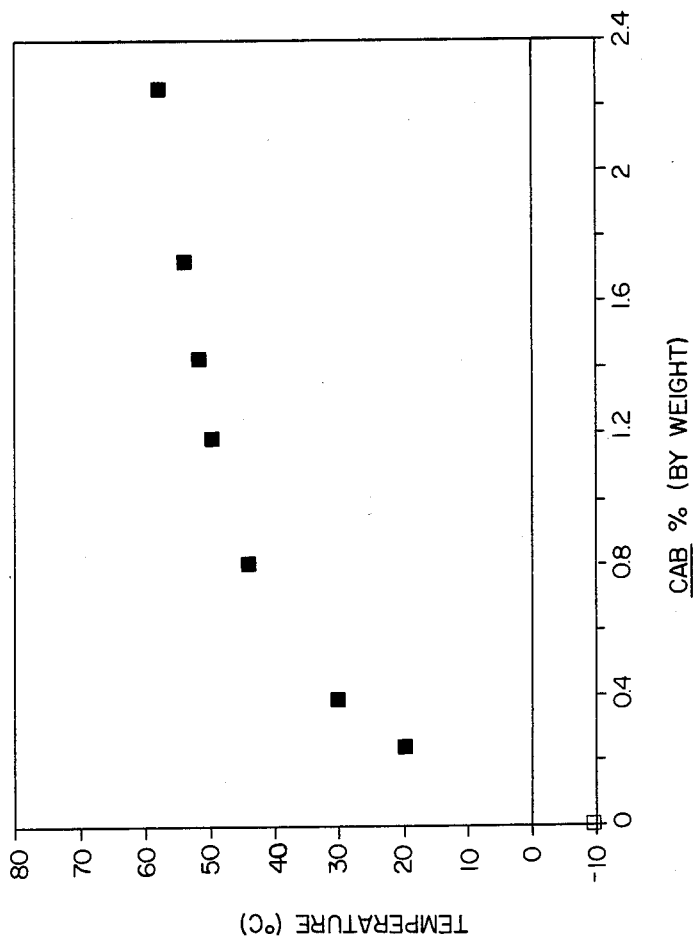
FIG. 4 is a graph plotting gellation temperature against CAB concentration in n-dodecane. The cyrstallization temperature of n-dodecane is shown as an unfilled square.

Gellation temperature versus CAB concentration profiles, as exemplified by n-dodecane in FIG. 4, have an initial rise region followed by a plateau. In the plateau region, n-alkanes (n-heptane, n-octane, n-dodecane, n-hexadecane) exhibit gellation temperatures which depend upon the concentration of CAB but not upon the alkane chain length. At 0.8% of CAB by weight, the n-alkanes exhibit a gellation temperature of 43°±2° C. Cyclohexane does not behave similarly and the stability of its gel is much lower than that of the n-alkanes.

The stability of the gels, as measured by their lifetimes at ambient temperatures, depends upon the concentration of CAB and the nature of the solvent. For instance, at 3–4% of CAB by weight in n-dodecane, the gels are very unstable. They rapidly become cloudy and then form crystals with attendant loss of their non-flowing characteristics. The most stable gels of CAB which we have observed employ 4-heptanol or heptanal as solvent. A mixture of 1.53% of CAB in heptanal in a closed vessel has remained a gel at ambient temperatures for more than eleven months. Gels with other solvents are stable for a few hours to a few weeks.

EXPERIMENTAL

Absorption spectra were obtained on a Perkin-Elmer UV/VIS spectrophotometer. Fluorescence spectra were recorded front-face or right angle on a Spex Fluorolog spectrofluorimeter (150 W/1 XBO high pressure xenon lamp) equipped with a Datamate computer. Gel solutions were sealed under reduced pressure in 0.8 mm (i.d.) Kimax cells. Optical microscopy was viewed through a Kofler hot-stage microscopy with plane polarizers above and below the sample stage. Circular dichroism spectra were recorded on a Jasco ORD/UV 5 spectrophotometer with a CD attachment. NMR spectra were obtained on a 90 MHz Fourier Transform Bruker FHX-10 spectrometer.

A pyrex filtered Hanovia 450 W medium mercury arc was employed in the preparative irradiations. Samples were degassed and sealed (3 freeze-pump-thaw cycles at $<10^{-4}$ torr) and then thermostatted in an aluminum block with a window to the lamp. Analyses of products were performed on a Water high performance liquid chromatograph (254 nm UV detection) using a Waters Radical Pak silica column and an 80/20 hexane/chloroform (Aldrich, ethanol stablized) mixture as eluent.

Having now fully described this invention, it will be apparent to one of ordinary skill in the art that many changes and modifications may be made thereto without departing from the spirit or scope of the invention as set forth herein.

What is claimed is:

1. A gelled organic solvent comprising a solvent selected from the group consisting of alkanes, alkenes, alkanols, aldehydes, acids, esters, and amines, in combination with a gel-producing amount of a compound having the formula (I)

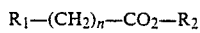

$$R_1-(CH_2)_n-CO_2-R_2 \quad (I)$$

wherein n is zero or a whole number between 2 and 20, $R_1$ is an anthracene analogue or substituted anthracene analogue, and $R_2$ is selected from the group consisting of cholesteryl, cholestanyl, and their derivatives.

2. The gelled organic solvent of claim 1 wherein the gelling agent is present in an amount of about 0.05–20 weight percent, based on the weight of said organic solvent.

3. The gelled organic solvent of claim 1 wherein said solvent is an alkane having 1 to 30 carbon atoms.

4. The gelled organic solvent of claim 1 wherein said solvent comprises an alkanol containing from 1 to 20 carbon atoms.

5. The gelled organic solvent of claim 1 wherein said organic solvent comprises fuel.

6. The gelled organic solvent of claim 1 wherein said anthracene analogue is selected from the group consisting of

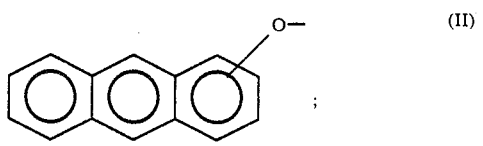

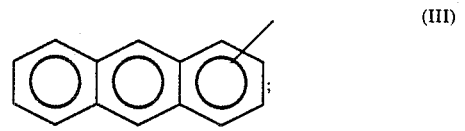

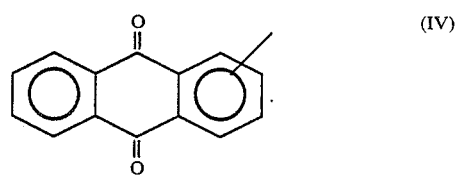

7. The gelled organic solvent of claim 1 wherein $R_2$ is cholesteryl.

8. The gelled organic solvent of claim 1 wherein $R_2$ is cholestanyl.

9. The gelled organic solvent of claim 1 wherein said compound comprises cholesteryl anthracene-2-carboxylate.

10. The gelled organic solvent of claim 1 wherein said compound comprises cholesteryl anthraquinone-2-carboxylate.

11. The gelled organic solvent of claim 1 wherein said compound comprises cholesteryl 4-(2-anthryloxy)-butanoate.

12. The gelled organic solvent of claim 1 wherein said compound comprises cholesteryl 5-(2-anthryloxy)pentanoate.

13. The gelled organic solvent of claim 1 wherein said compound comprises 6-ketocholestanyl 4-(2-anthryloxy)butanoate.

14. The gelled organic solvent of claim 1, wherein said anthracene analogue or substituted anthracene analogue is linked at the 2-position thereof and said cholesteryl, cholestanyl or their derivatives are linked at the 3-position thereof.

15. A process for producing a gelled organic solvent comprising mixing said organic solvent with a gell producing amount of a gelling agent having the formula $$R_1\text{—}(CH_2)_n\text{—}CO_2\text{—}R_2,$$

wherein n is zero or a whole number between 2 and 20, $R_1$ is an anthracene analogue, and $R_2$ is selected from the group consisting of cholesteryl, cholestanyl, and their derivatives.

16. The process of claim 15 wherein said gelling agent is present in an amount of about 0.1–20% based on the weight of the organic solvent.

17. The process of claim 15 wherein said gelling agent is added to said solvent at an elevated temperature and the resulting composition then cooled to effect gelling.

18. The process of claim 15, wherein said anthracene analogue or substituted anthracene analogue is linked at the 2-position thereof and said cholesteryl, cholestanyl or their derivatives are linked at the 3-position thereof.

* * * * *